United States Patent [19]

Riebel et al.

[11] 4,396,416
[45] Aug. 2, 1983

[54] N-ACYL-PIPERIDON COMPOUNDS AND THEIR USE AS ANTIDOTES FOR PROTECTING CROP PLANTS FROM HERBICIDAL DAMAGE

[75] Inventors: Hans-Jochem Riebel, Wuppertal; Ludwig Eue, Leverkusen; Wilfried Faust, Odenthal, all of Fed. Rep. of Germany

[73] Assignee: Bayer Aktiengesellschaft, Leverkusen, Fed. Rep. of Germany

[21] Appl. No.: 252,982

[22] Filed: Apr. 10, 1981

Related U.S. Application Data

[62] Division of Ser. No. 184,728, Sep. 8, 1980, Pat. No. 4,294,967.

[30] Foreign Application Priority Data

Sep. 21, 1979 [DE] Fed. Rep. of Germany ....... 2938155

[51] Int. Cl.³ ............................................ A01N 25/32
[52] U.S. Cl. .......................................... 71/92; 71/94; 71/100; 71/118

[58] Field of Search ....................... 71/94, 92; 546/242

[56] References Cited

FOREIGN PATENT DOCUMENTS 2218097 12/1971 Fed. Rep. of Germany .

*Primary Examiner*—Catherine L. Mills
*Attorney, Agent, or Firm*—Felfe & Lynch

[57] ABSTRACT

N-Acyl-piperidones of the formula

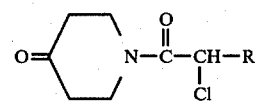

wherein R represents methyl or chloro, and their use as antidotes for protecting crop plants from herbicidal damage.

9 Claims, No Drawings

N-ACYL-PIPERIDON COMPOUNDS AND THEIR USE AS ANTIDOTES FOR PROTECTING CROP PLANTS FROM HERBICIDAL DAMAGE

This is a division of Ser. No. 184,728 filed on Sept. 8, 1980, now U.S. Pat. No. 4,294,967.

This invention relates to certain new N-acyl-piperidone compounds and to their use as antidotes for protecting crop plants from herbicidal damage, especially by herbicidally active thiolcarbamates and acetanilides. The invention further relates to new active compound combinations of the N-acyl-piperidone compounds and certain herbicidally active carbamates and acetanilides which have particularly good selective herbicidal properties.

"Antidotes" ("safeners") in the present connection are to be understood as substances which are capable of specifically antagonising the harmful effects of herbicides on crop plants, that is to say of protecting the crop plants, without thereby noticeably influencing the herbicidal action on the weeds to be combated.

It is known that, when used for combating weeds in maize and other crops, certain thiolcarbamates and acetanilides cause damage to the crop plants to a greater or lesser extent. It is furthermore known that such compounds as, for example, N-dichloroacetyl-2-ethylpiperidine and N-dichloroacetyl-cis/trans-decahydroquinoline are suitable for reducing damage to crop plants by thiolcarbamates or acetanilides (see DE-OS (German Published Specification) No. 2,218,097). However, the activity of these substances as antidotes is not always completely satisfactory.

The present invention now provides, as new compounds, the N-acyl-piperidones of the general formula

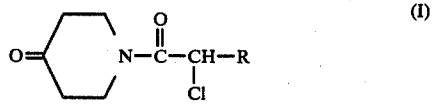

in which R represents methyl or chloro.

The invention also provides a process for the preparation of a N-acyl-piperidone of the formula (I) in which piperidone-(4) of the formula

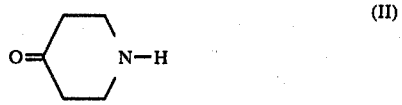

or its hydrochloride is reacted with alkanoyl chlorides of the formula

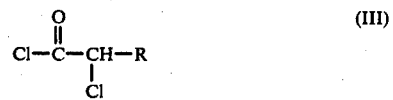

in which R has the meaning indicated above, if appropriate in the presence of a diluent and if appropriate in the presence of an acid-binding agent.

It has been found that N-acyl-piperidones of the formula (I) are outstandingly suitable for protecting crop plants from damage by herbicidally active thiolcarbamates or by herbicidally active acetanilides.

It has also been found that the new active compound combinations comprising an N-acyl-piperidone of the formula (I) and at least one herbicidally active thiolcarbamate and/or at least one herbicidally active acetanilide are outstandingly suitable for selectively combating weeds in crops of useful plants.

Surprisingly, herbicidal damage to crop plants by thiolcarbamates or by acetanilides is better suppressed when N-acyl-piperidones of the formula (I) are also used than when the known compounds N-dichloroacetyl-2-ethyl-piperidine and N-dichloroacetyl-cis/trans-decahydroquinoline, which are chemically similar substances of the same type of action, are employed. Moreover, it was not to be expected that the active compound combinations according to the invention have better selective herbicidal properties than active compound combinations which consist of at least one herbicidally active thiolcarbamate or at least one herbicidally active acetanilide and N-dichloroacetyl-2-ethylpiperidine, which is known as an antidote, or N-dichloroacetyl-cis/trans-decahydroquinoline, which is likewise known as an antidote.

If piperidone-(4)-hydrochloride hydrate and dichloroacetylchloride are used as starting substances, the course of the process according to the invention can be represented by the following equation:

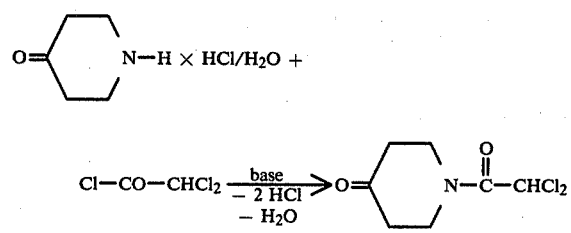

The piperidone-(4) of the formula (II), which is required as starting substance in the process according to the invention, is already known (compare Koenigs, Neumann; Ber.dtsch.chem. Ges. 48 (1915)960). The alkanoyl chlorides of the formula (III), which are required as reaction components in the process according to the invention, are known as well (compare DE-OS (German Published Specification) No. 2,218,097).

The process for the preparation of the N-acyl-piperidones of the formula (I) is preferably carried out in the presence of a diluent. Diluents which can be used in this process are water and inert organic solvents. These solvents include, as preferences, ketones, such as diethyl ketone and methyl isobutyl ketone; nitriles, such as propionitrile and acetonitrile; ethers, such as tetrahydrofuran or dioxan; aliphatic and aromatic hydrocarbons, such as petroleum ether, benzene, toluene and xylene; halogenated hydrocarbons, such as methylene chloride, carbon tetrachloride, chloroform or chlorobenzene; esters, such as ethyl acetate; and formamides, such as, in particular, dimethylformamide.

Possible acid-binding agents for carrying out the above-mentioned process are any customary acid acceptors.

These include, as preferences, alkali metal hydroxides, such as sodium hydroxide and potassium hydroxide, alkali metal carbonates, such as sodium carbonate, potassium carbonate and sodium bicarbonate, and lower tertiary amines, such as triethylamine, dimethylbenzylamine, pyridine, diazabicyclooctane and 1,8-diaza-bicyclo[5.4.0]undec-7-ene. However, piperidone of the formula (II) employed in excess can also simultaneously function as the acid-binding agent. In this case, it is not necessary to add an additional acid-binding agent.

The reaction temperatures can be varied within a substantial range in the above-mentioned process. In general, the reaction is carried out between 0° and 100° C., preferably between 10° and 80° C.

In carrying out the above-mentioned process, 1 to 2 mols of alkanoyl chloride of the formula (III) and, if appropriate, 1 to 2 mols of acid-binding agent are preferably employed per 1 mol of piperidone-(4) of the formula (II). The isolation of the reaction products is effected by customary methods. In general, a procedure is followed in which, when the reaction has ended, water is added to the reaction mixture, the organic phase is separated, the aqueous phase is extracted several times with an organic solvent, the combined organic phases are dried and concentrated.

As already mentioned, the N-acyl-piperidones of the formula (I) are suitable for protecting crop plants from damage by herbicidally active thiolcarbamates and acetanilides without noitceably influencing their herbicidal action.

The N-acyl-piperidones of the formula (I) can preferably be used as antidotes for protecting crop plants from damage by herbicidally active thiolcarbamates of the general formula

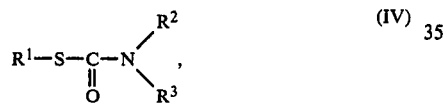

in which
  $R^1$ represents lower alkyl, benzyl, chlorobenzyl or alkoxybenzyl and
  $R^2$ and $R^3$ independently of one another represent alkyl with 2 to 4 carbon atoms or cyclohexyl, or $R^2$ and $R^3$, together with the adjacent nitrogen atom, represent a five-membered to seven-membered heterocyclic ring, and for protecting crop plants from damage by herbicidally active acetanilides of the general formula

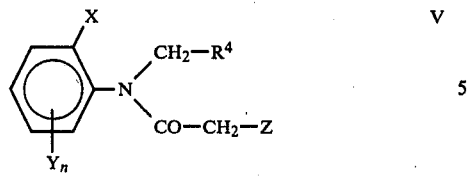

in which
  $R^4$ represents an optionally substituted N-containing heterocyclic radical,
  X and Y are identical or different and represent alkyl,
  Z represents halogen and
  n represents 0, 1 or 2,
and herbicidally active acid-addition salts and metal salt complexes thereof, and of the general formula

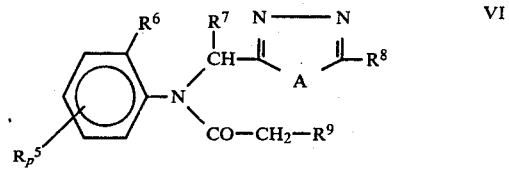

in which
  A represents oxygen, sulphur or the grouping $>NR^{10}$,
  $R^7$ represents hydrogen or alkyl,
  $R^8$ represents hydrogen, alkyl, haloalkyl, alkenyl, alkynyl, cycloalkyl, halogen, optionally substituted aryl, optionally substituted aralkyl or the grouping $-OR^{11}$, $-SR^{11}$ or $NR^{10}R^{11}$,
  $R^{10}$ represents hydrogen, alkyl or optionally substituted aryl,
  $R^{11}$ represents hydrogen, alkyl, haloalkyl, alkenyl, alkynyl, cycloalkyl or optionally substituted aralkyl,
  $R^5$ represents alkyl,
  $R^6$ represents alkyl or halogen,
  $R^9$ represents halogen and
  p represents 0, 1 or 2,
and of the formula

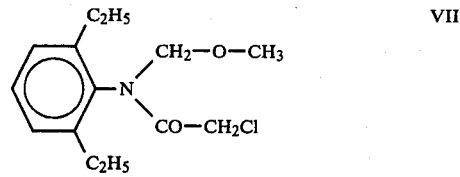

and of the formula

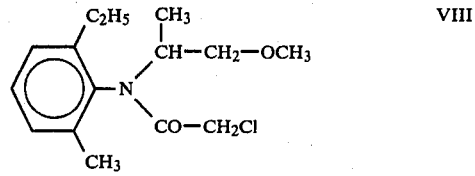

Specific examples of thiolcarbamates of the formula IV which may be mentioned are: S-ethyl N,N-dipropylthiocarbamate, S-ethyl N,N-diisobutylthiocarbamate, S-propyl N-butyl-N-ethylthiocarbamate, S-propyl N,N-diisopropylthiocarbamate, S-ethyl N,N-diethylthiocarbamate, S-ethyl N-ethyl-N-cyclohexylthiocarbamate, S-ethyl hexadro-azepine-1-thiocarbamate, S-p-methoxybenzyl N,N-diethylthiocarbamate, S-p-chlorobenzyl N,N-diethylthiocarbamate, S-benzyl N,N-diethylthiocarbamate, S-benzyl N,N-di-sec.-butylthiocarbamate and S-propyl N-ethyl-N-butylthiocarbamate.

The thiolcarbamates of the formula IV and their herbicidal activity are already known (see U.S. Pat. Nos. 2,913,327, 3,037,853, 3,185,720, 3,198,786 and 3,582,314).

In the formula V, $R^4$ preferably represents an optionally substituted radical selected from pyrazol-1-yl, imidazol-1-yl, 1,2,4-triazol-1-yl, 1,2,3-triazol-1-yl, 1,3,4-triazol-1-yl, 1,2,3,4-tetrazol-1-yl and pyrrol-1-yl. Preferred substituents are: halogen (especially fluorine, chlorine and bromine) and alkyl with 1 to 4 carbon atoms. X and Y are identical or different and preferably represent straight-chain or branched alkyl with 1 to 4 carbon atoms. Z preferably represents chlorine or bromine and the index n represents 0, 1 or 2.

Specific examples of acetanilides of the formula V which may be mentioned are: 2-methyl-6-ethyl-N-(pyrazol-1-yl-methyl)-chloroacetanilide, 2,6-diethyl-N-(pyrazol-1-yl-methyl)-chloroacetanilide, 2,6-diethyl-N-(1,2,4-triazol-1-yl-methyl)-chloroacetanilide, 2,6-dimethyl-N-(1,2,4-triazol-1-yl-methyl)-chloroacetanilide, 2-methyl-N-(pyrazol-1-yl-methyl)-chloroacetanilide, 2,5-dimethyl-N-(pyrazol-1-yl-methyl)-chloroacetanilide, 2,3-dimethyl-N-(pyrazol-1-yl-methyl)-chloroacetanilide, 2-methyl-6-ethyl-N-(pyrazol-1-yl-methyl)-chloroacetanilide hydrochloride, 2,6-diethyl-N-(pyrazol-1-yl-methyl)-chloroacetanilide hydrochloride, 2,6-diethyl-N-[(3,5-dimethyl-pyrazol-1-yl)-methyl]-chloroacetanilide, 2,6-diethyl-N-[(3-chloro-1,2,4-triazolyl)-methyl]-chloroacetanilide, 2-methyl-6-ethyl-N-[(3,5-dimethyl-pyrazol-1-yl)-methyl]-chloroacetanilide, 2-tert.-butyl-N-(pyrazol-1-yl-methyl)-chloroacetanilide, 2-methyl-6-ethyl-N-[(3-bromo-5-methyl-pyrazol-1-yl)-methyl]-chloroacetanilide, 2-methyl-6-ethyl-N-[(3-chloro-1,2,4-triazolyl)-methyl]-chloroacetanilide and 2,6-diethyl-N-[(4-chloro-pyrazol-1-yl)-methyl]-chloroacetanilide.

Further preferred acetanilides of the formula V are listed in the following Table 1.

TABLE 1

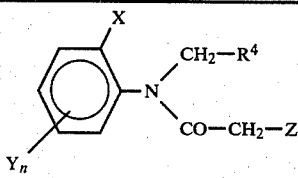

| Example No. | X | $Y_n$ | Z | $R^4$ |
|---|---|---|---|---|
| V-1 | $C_2H_5$ | 6-$C_2H_5$ | Cl | Pyrazol-1-yl |
| V-2 | $C_2H_5$ | 6-$C_2H_5$ | Cl | 1,2,4-Triazol-1-yl |
| V-3 | i-$C_3H_7$ | 6-i-$C_3H_7$ | Cl | Pyrazol-1-yl |
| V-4 | $CH_3$ | 6-$C_2H_5$ | Cl | 1,2,4-Triazol-1-yl |
| V-5 | $CH_3$ | 6-$C_2H_5$ | Cl | Pyrazol-1-yl |
| V-6 | $C_2H_5$ | 4,6-$(CH_3)_2$ | Cl | Pyrazol-1-yl |
| V-7 | $CH_3$ | 4,6-$(CH_3)_2$ | Cl | Pyrazol-1-yl |
| V-8 | $C_2H_5$ | 4-$CH_3$, 6-$C_2H_5$ | Cl | Pyrazol-1-yl |
| V-9 | i-$C_3H_7$ | 6-i-$C_3H_7$ | Cl | 1,3,4-Triazol-1-yl |
| V-10 | i-$C_3H_7$ | 6-i-$C_3H_7$ | Cl | 1,2,4-Triazol-1-yl |
| V-11 | $C_2H_5$ | 6-$C_2H_5$ | Cl | Pyrrol-1-yl |
| V-12 | i-$C_3H_7$ | — | Cl | 1,2,4-Triazol-1-yl |
| V-13 | $CH_3$ | 6-$C_2H_5$ | Cl | 1,2,3,4-Tetrazol-1-yl |
| V-14 | i-$C_3H_7$ | — | Cl | Pyrazol-1-yl |
| V-15 | $C_2H_5$ | — | Cl | 1,2,4-Triazol-1-yl |
| V-16 | $CH_3$ | 6-$CH_3$ | Cl | Pyrazol-1-yl |
| V-17 | $CH_3$ | 6-$CH_3$ | Cl | 1,2,4-Triazol-1-yl |
| V-18 | $CH_3$ | 5-$CH_3$ | Cl | 1,2,4-Triazol-1-yl |
| V-19 | $CH_3$ | — | Cl | Pyrazol-1-yl |
| V-20 | $CH_3$ | — | Cl | 1,2,4-Triazol-1-yl |
| V-21 | $CH_3$ | 5-$CH_3$ | Cl | Pyrazol-1-yl |
| V-22 | $CH_3$ | 3-$CH_3$ | Cl | 1,2,4-Triazol-1-yl |
| V-23 | $CH_3$ | 3-$CH_3$ | Cl | Pyrazol-1-yl |
| V-24 | $C_2H_5$ | 6-$CH_3$ | Cl | Pyrazol-1-yl (×HCl) |
| V-25 | $C_2H_5$ | 6-$C_2H_5$ | Cl | Pyrazol-1-yl (×HCl) |
| V-26 | $C_2H_5$ | 6-$C_2H_5$ | Cl | 3,5-Dimethyl-pyrazol-1-yl |
| V-27 | $C_2H_5$ | 6-$C_2H_5$ | Cl | Bromomethyl-pyrazolyl |
| V-28 | $C_2H_5$ | 6-$C_2H_5$ | Cl | 3-Chloro-1,2,4-triazol-1-yl |
| V-29 | $CH_3$ | 6-$C_2H_5$ | Cl | 3,5-Dimethyl-pyrazol-1-yl |
| V-30 | $C_2H_5$ | 6-$C_2H_5$ | Cl | 3-Methyl-pyrazol-1-yl |
| V-31 | $C_2H_5$ | 6-$CH_3$ | Cl | 3-Methyl-pyrazol-1-yl |
| V-32 | $C(CH_3)_3$ | — | Cl | Pyrazol-1-yl |
| V-33 | $C(CH_3)_3$ | — | Cl | 1,2,4-Triazol-1-yl |
| V-34 | $C_2H_5$ | 6-$CH_3$ | Cl | Bromo-methyl-pyrazolyl |
| V-35 | $CH_3$ | 6-$C_2H_5$ | Cl | 4-Chloro-pyrazol-1-yl |

TABLE 1-continued

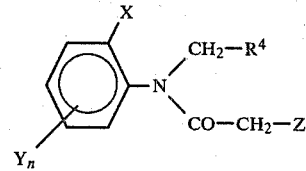

| Example No. | X | $Y_n$ | Z | $R^4$ |
|---|---|---|---|---|
| V-36 | $CH_3$ | 6-$C_2H_5$ | Cl | 3-Chloro-1,2,4-triazol-1-yl |
| V-37 | $C_2H_5$ | 6-$CH_3$ | Cl | 2,4,5-Trichloro-imidazol-1-yl |
| V-38 | $C_2H_5$ | 6-$C_2H_5$ | Cl | 4-Chloro-pyrazol-1-yl |
| V-39 | $C_2H_5$ | 6-$C_2H_5$ | Cl | 1,2,3,4-Tetrazol-1-yl |
| V-40 | $C_2H_5$ | 6-$C_2H_5$ | Br | Pyrazol-1-yl |
| V-41 | $CH_3$ | 6-$C_2H_5$ | Br | Pyrazol-1-yl |
| V-42 | $C_2H_5$ | 6-$C_2H_5$ | Cl | Imidazol-1-yl |
| V-43 | $C_2H_5$ | 6-$C_2H_5$ | Br | 1,2,4-Triazol-1-yl |
| V-44 | $CH_3$ | 6-$C_2H_5$ | Br | 1,2,4-Triazol-1-yl |

The acetanilides of the formula V and their herbicidal activity, and herbicidally active acid addition salts and metal salt complexes thereof are already known (see DE-OS (German Published Specification) No. 2,648,008 (German Published Specification) No. 2,704,281).

In the formula VI, A preferably represents oxygen, sulphur or the grouping —$NR^{10}$, wherein $R^{10}$ represents hydrogen, straight-chain or branched alkyl with 1 to 4 carbon atoms or aryl with 6 to 10 carbon atoms (especially phenyl), it being possible for the aryl radical to carry one or more substituents selected from halogen, alkyl with 1 to 4 carbon atoms, alkoxy with 1 or 2 carbon atoms, alkylthio with 1 or 2 carbon atoms, cyano, nitro and haloalkyl with up to 2 carbon atoms and up to 5 identical or different halogen atoms (preferred halogens being fluorine or chlorine). $R^7$ preferably represents hydrogen or methyl. $R^8$ in the formula VI preferably represents hydrogen, straight-chain or branched alkyl with 1 to 4 carbon atoms, haloalkyl with up to 3 carbon atoms and up to 5 identical or different halogen atoms (preferred halogens being fluorine or chlorine, and trifluoromethyl being mentioned as an example), alkenyl or alkynyl with in either case 2 to 4 carbon atoms, cycloalkyl with 5 to 7 carbon atoms or halogen (especially fluorine, chlorine or bromine). $R^8$ furthermore preferably represents aryl with 6 to 10 carbon atoms (especially phenyl), it being possible for the aryl radical to carry one or more substituents selected from halogen, alkyl with 1 to 4 carbon atoms, alkoxy with 1 or 2 carbon atoms, alkylthio with 1 or 2 carbon atoms, cyano, nitro and haloalkyl with up to 2 carbon atoms and up to 5 identical or different halogen atoms (preferred halogens being fluorine or chlorine and trifluoromethyl being mentioned as a specific example of haloalkyl). $R^8$ furthermore preferably represents aralkyl with 6 to 10 carbon atoms in the aryl part and 1 to 4 carbon atoms in the alkyl part (especially benzyl), it being possible for the aralkyl radical to carry, on the aryl part, one or more substituents selected from halogen, alkyl with 1 to 4 carbon atoms, alkoxy with 1 or 2 carbon atoms, alkylthio with 1 or 2 carbon atoms, cyano, nitro and haloalkyl with up to 2 carbon atoms and up to 5 identical or different halogen atoms (preferred halogens being fluorine or chlorine, and trifluoromethyl being mentioned as a specific example of haloalkyl). $R^8$ also preferably represents the grouping —$OR^{11}$, —$SR^{11}$ or —NR$^{10}$R$^{11}$, wherein R$^{10}$ has the preferred meanings which have already been mentioned above for this radical, and R$^{11}$ represents hydrogen, straight-chain or branched alkyl with 1 to 4 carbon atoms, haloalkyl with 1 to 3 carbon atoms and up to 5 identical or different halogen atoms (preferred halogens being fluorine and chlorine, and trifluoromethyl being mentioned as an example), alkenyl or alkynyl with in either case 2 to 4 carbon atoms, cycloalkyl with 5 to 7 carbon atoms or aralkyl with 6 to 10 carbon atoms in the aryl part and 1 to 4 carbon atoms in the alkyl part (especially benzyl), it being possible for the aralkyl radical to carry, on the aryl part, one or more substituents selected from halogen, alkyl with 1 to 4 carbon atoms, alkoxy with 1 or 2 carbon atoms, alkylthio with 1 or 2 carbon atoms, cyano, nitro and haloalkyl with up to 2 carbon atoms and up to 5 identical or different halogen atoms (preferred halogens being fluorine or chlorine, and trifluoromethyl being mentioned as a specific example of haloalkyl). In the formula III, R$^5$ preferably represents straight-chain or branched alkyl with 1 to 4 carbon atoms, R$^6$ preferably represents straight-chain or branched alkyl with 1 to 4 carbon atoms, fluorine, chlorine or bromine, and R$^9$ preferably represents chlorine, bromine or iodine. The index p represents 0, 1 or 2.

Specific examples of acetanilides of the formula VI which may be mentioned are: 2,6-diethyl-N-[(2-methyl-1,3,4-oxadiazol-5-yl)-methyl]-chloroacetanilide, 2,6-dimethyl-N-[(2-methyl-1,3,4-oxadiazol-5-yl)-methyl]-chloroacetanilide, 2-ethyl-6-methyl-N-[(2-methyl-1,3,4-oxadiazol-5-yl)-methyl]-chloroacetanilide and 2-tert.-butyl-N-[(2-methyl-1,3,4-oxadiazol-5-yl)-methyl]-chloroacetanilide.

Further preferred acetanilides of the formula VI, are listed in the following Table 2.

TABLE 2

(VI)

| Example No. | R$^7$ | R$^8$ | R$^6$ | R$_p^5$ | A | R$^9$ |
|---|---|---|---|---|---|---|
| VI-1 | H | CH$_3$ | CH$_3$ | 6-C$_2$H$_5$ | O | Cl |
| VI-2 | H | SCH$_3$ | C$_2$H$_5$ | 6-C$_2$H$_5$ | N—CH$_3$ | Cl |
| VI-3 | H | CH$_3$ | C$_2$H$_5$ | 6-C$_2$H$_5$ | O | Cl |
| VI-4 | H | CH$_3$ | CH$_3$ | 6-CH$_3$ | O | Cl |
| VI-5 | H | CH$_3$ | C(CH$_3$)$_3$ | — | O | Cl |
| VI-6 | H | —S—CH$_2$—CH=CH$_2$ | C$_2$H$_5$ | 6-C$_2$H$_5$ | 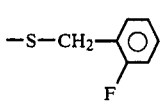 | Cl |
| VI-7 | H |  | CH$_3$ | 6-C$_3$H$_5$ | 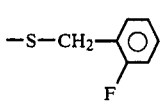 | Cl |
| VI-8 | H | C$_2$H$_5$ | CH$_3$ | 6-C$_2$H$_5$ | O | Cl |
| VI-9 | H | C$_2$H$_5$ | C$_2$H$_5$ | 6-C$_2$H$_5$ | O | Cl |
| VI-10 | H | i-C$_3$H$_7$ | CH$_3$ | 6-C$_2$H$_5$ | O | Cl |
| VI-11 | H | CH$_3$ | CH$_3$ | 3-CH$_3$ | 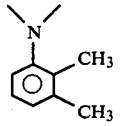 | Cl |
| VI-12 | H | CH$_3$ | C$_2$H$_5$ | 6-C$_2$H$_5$ | O | Br |
| VI-13 | H | CH$_3$ | CH$_3$ | 6-C$_2$H$_5$ | O | Br |
| VI-14 | H | CH$_3$ | i-C$_3$H$_7$ | 6-i-C$_3$H$_7$ | O | Cl |

The acetanilides of the formula (VI) and their herbicidal activity are already known (compare DE-OS (German Published Specification) No. 2,805,757).

Further preferred acetanilides with which the compounds of the formula (I) according to the invention can be employed as antidotes are the compounds of the formulae (VII) and (VIII). These substances and their herbicidal activity are already known (see U.S. Pat. No. 3,442,945 and DE-OS (German Published Specification) No. 2,328,340).

The N-acyl-piperidones of the formula (I) according to the invention are particularly suitable for protecting important crop plants, such as maize, soya bean, cotton, sugar beet, cereals, rice and cane sugar, from herbicidal damage by thiolcarbamates and acetanilides.

The active compound combinations according to the invention, which comprise an N-acyl-piperidone of the formula (I) and at least one herbicidally active thiolcarbamate and/or at least one herbicidally active acetanilide, exhibit a very good action against broadleaved weeds and graminaceous weeds in numerous crops of useful plants. They can therefore be used for selectively combating weeds in numerous crops of useful plants. By weeds, in the broadest sense, there are to be understood in this context all plants which grow in locations where they are undesired.

The active compound combinations according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compound combinations according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, and Cucurbita; and monocotyledon cultures of the genera Oryza, Zea, Triticum, Hordeum, Avena, Secale, Sorghum, Panicum, Saccharum, Ananas, Asparagus and Allium.

The active compound combinations according to the invention are particularly suitable for selectively combating weeds in maize, soya bean, cotton, sugar beet, cereals, rice and cane sugar. The antidotes according to the invention can be converted, if appropriate as a mixture with the herbicidal active compounds with which they are employed, into the customary formulations, such as solutions, emulsions, wettable powders, suspensions, powders, dusting agents, foams, pastes, soluble powders, granules, suspension-emulsion concentrates, natural and synthetic materials impregnated with active compound, very fine capsules in polymeric substances and in coating compositions, for use on seed.

These formulations are produced in known manner, for example by mixing the antidotes according to the invention, if appropriate as a mixture with the herbicidal active compounds with which they are employed, with extenders, that is to say liquid or solid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulfifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain between 0.1 and 95% by weight of antidote or antidote and herbicidal active compound, preferably between 0.5 and 90%.

The antidotes according to the invention, as such or in the form of their formulations, can, as stated above, also be employed as mixtures with herbicidal active compounds, finished formulations or tank mixing being possible. Mixtures with other active compounds, such as fungicides, insecticides, acaricides, nematicides, bird repellants, growth factors, plant nutrients and agents which improve soil structure are also possible.

The antidotes according to the invention or mixtures of the antidotes according to the invention and a herbicidal active compound can be employed as such, in the form of their formulations or in the use forms prepared therefrom by further dilution, such as ready-to-use solutions, suspensions, emulsions, powders and granules. They may be used in the customary manner, for example by watering, spraying, atomizing, dusting or scattering, dry dressing, moist dressing, wet dressing, slurry dressing or encrusting.

The antidotes according to the invention can be applied by methods customary for antidotes of this type. Thus, the antidotes according to the invention can be applied either before or after the herbicide, or can be applied together with the herbicide. If the herbicide is used before or after sowing, crop plants can also be protected from damage by treating the seed with the antidotes before sowing (dressing). A further possible way of using the antidotes is to apply them to the seed furrow during sowing. If the plants are seedlings, these can be treated with the antidotes before being transplanted.

When the antidotes according to the invention are employed, the customary amounts, at the location, of the particular herbicides are applied. The amounts of herbicidal active compound used vary between 0.5 and 5 kg/ha. The amount of antidote used is independent of the herbicide and of the amount of herbicidal active compound used. In general, the amounts of antidotes according to the invention applied are between 0.1 and 5 kg/ha in the case of treatment of the soil surface, preferably between 0.2 and 4 kg/ha. In the case of seed treatment, the amounts of antidotes according to the invention applied are in general between 10 and 300 g per kilogram of seed, preferably between 25 and 200 g per kilogram of seed.

The weight ratios of antidotes to herbicidal active compounds in the active compound combinations according to the invention can vary within relatively wide limits. In general, 0.04 to 1.0 part by weight, preferably 0.1 to 0.5 part by weight, of antidote of the formula (I) is present per 1 part by weight of herbicidal active compound.

Thus, the present invention also provides an antidote composition containing as active ingredient a compound of the formula (I) in admixture with a solid diluent or carrier or in admixture with a liquid diluent or carrier containing a surface-active agent.

The present invention also provides a method of protecting crop plants from damage by herbicidally active thiolcarbamates or herbicidally active acetanilides in which there is applied to the plants, or to a habitat thereof, a compound of the formula (I) alone or in the form of a composition containing as active ingredient a compound of the formula (I) in admixture with a diluent or carrier.

The present invention also provides crops protected from damage by herbicidally active thiolcarbamates or by herbicidally active acetanilides by being grown in areas in which immediately prior to and/or during the time of the growing a compound of the formula (I) was applied, alone or in admixture with a diluent or carrier.

The present invention also provides a herbicidal composition that contains as active ingredients (1) a compound of the formula (I) and (2) at least one herbicidally active compound selected from thiolcarbamates and acetanilides, alone or in admixture with a solid or liquid diluent or carrier.

The present invention also provides a method of combating weeds, in which there is applied to the weeds, or to a habitat thereof, a herbicidal composition according to the present invention.

The present invention further provides crops protected from damage by weeds by being grown in areas in which immediately prior to and/or during the time of the growing, a herbicidal composition of the present invention was applied.

It will be seen that the usual methods of providing a harvested crop may be improved by the present invention.

PREPARATIVE EXAMPLES

EXAMPLE 1

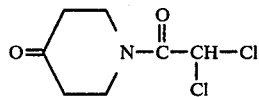

First of all 30.4 g (0.2 mol) of 1.8-diaza-bicyclo[5.4.0]undec-7-ene in 50 ml of acetonitrile followed by 14.7 g (0.1 mol) of dichloroacetyl chloride were added dropwise to a solution of 15.4 g (0.1 mol) of piperidone-(4)-hydrochloride hydrate in 150 ml of acetonitrile at 20° C. The reaction mixture was subsequently stirred at 20°-25° C. for 5 hours. Thereafter, the reaction mixture was poured into 400 ml of water. The aqueous solution was extracted twice with 100 ml of toluene in each case. The combined toluene extracts were dried over sodium sulphate and then concentrated. 14 g (66.6% of theory) of N-dichloroacetyl-piperidone-(4) were obtained in this manner in the form of yellow crystals of melting point 85°-87° C.

EXAMPLE 2

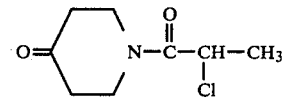

N-α-chloropropionyl)-piperidone-(4) was obtained in the form of yellow crystals of melting point 52° C. by reacting piperidone-(4)-hydrochloride hydrate with α-chloro-propionic acid chloride according to the method described in Example 1. Yield: 50% of theory.

The good activity of the antidotes according to the invention can be seen from the example which follows.

In this example, the compounds indicated below are employed as comparison compounds:

(A) = 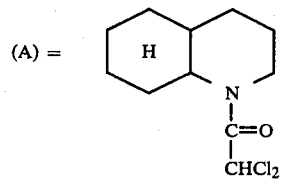

(N—Dichloroacetyl-cis/trans-decahydroquinoline)

(B) = 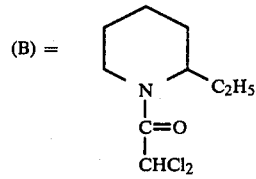

(N—Dichloroacetyl-2-ethyl-piperidine)

Furthermore, the acetanilide indicated below is employed as the herbicidal active compound in this example:

(C) = 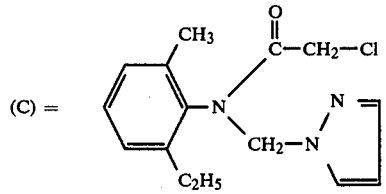

(2-Methyl-6-ethyl-N—(pyrazol-1-yl-methyl)-chloroacetanilide).

Example A

Pre-emergence Test

Solvent: 5 parts by weight of acetone
Emulsifier: 1 part by weight of alkylaryl polyglycol ether To produce a suitable preparation of active compound, 1 part by weight of herbicidal active compound or antidote, or of a mixture of antidote and herbicidal compound, was mixed with the stated amount of solvent, the stated amount of emulsifier was added and the concentrate was diluted with water to the desired concentration.

Seeds of the test plants were sown in normal soil and, after 24 hours, watered with the herbicide preparation or antidote preparation or with the preparation of antidote and herbicidal active compound. It was expedient to keep constant the amount of water per unit area. The concentration of the active compound in the preparation was of no importance, only the amount of active compound applied per unit area being decisive. After three weeks, the degree of damage to the plants was rated in % damage in comparison to the development of the untreated control. The figures denoted:

0% = no action (like untreated control)
100% = total destruction

Evaluation of the test results showed that the compound (1) (see preparative Example 1) was more suitable for protecting crop plants from damage by the compound (C) than the comparison compounds (A) and (B).

It will be understood that the specification and examples are illustrative, but no limitative of the present invention and that other embodiments within the spirit and scope of the invention will suggest themselves to those skilled in the art.

What is claimed is:

1. Method for the protection of maize from damage by herbicidally active acetanilides of the formula

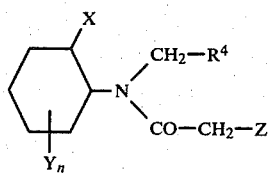

in which
R⁴ is pyrazol-1-yl or pyrazol-1-yl substituted by one or more radicals selected from fluorine, chlorine, bromine and alkyl with one to four carbon atoms,
X and Y are identical or different and represent alkyl with one to four carbon atoms,
Z represents halogen and
n represents 0, 1 or 2,
which method comprises applying to the maize plants or to their habitat, an antidotally effective amount of an N-acyl-piperidone compound of the formula

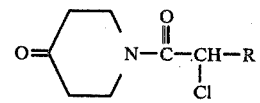

wherein R is methyl or chloro.

2. Method as claimed in claim 1 wherein said compound is applied to an area of agriculture in an amount of from 0.1 to 5 kg per hectare.

3. Method as claimed in claim 1 wherein said compound is applied to seed in an amount of 10 to 300 grams per kg of seed.

4. Method as claimed in claim 1 wherein said antidotal compound is selected from
N-dichloroacetyl-piperid-4-one and
N-(α-chloropropionyl)-piperid-4-one.

5. Herbicidal composition comprising an herbicidally active compound selected from acetanilide herbicides of the formula

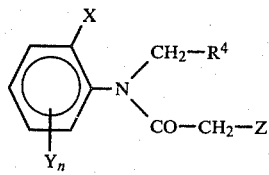

in which
R⁴ is pyrazol-1-yl or pyrazol-1-yl substituted by one or more radicals selected from fluorine, chlorine, bromine and alkyl with one to four carbon atoms,
X and Y are identical or different and represent alkyl, with one to four carbon atoms,
Z represents halogen and
n represents 0, 1 or 2, and, as an antidote, an effective amount of an N-acyl-piperidone compound of the formula

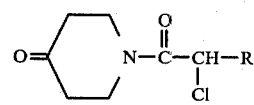

wherein R is methyl or chloro.

6. Herbicidal composition as claimed in claim 5 containing from 0.1 to 95% of a mixture consisting of an N-acyl-piperidone compound and a herbicidally active compound selected from thiolcarbamates and acetanilide herbicides.

7. Herbicidal composition as claimed in claim 5 containing from 0.04 to 1 part by weight of said antidote compound per part by weight of said herbicidally active compound.

8. Herbicidal composition as claimed in claim 5 containing from 0.1 to 0.5 part by weight of said antidote compound per part by weight of said herbicidally active compound.

9. Herbicidal composition as claimed in claim 5 wherein said antidotal compound is selected from
N-dichloroacetyl-piperid-4-one and
N-(α-chloropropionyl)-piperid-4-one.

* * * * *